May 20, 1958 D. H. MOREY, JR Plant Pat. 1,709
ROSE PLANT
Filed Sept. 19, 1957
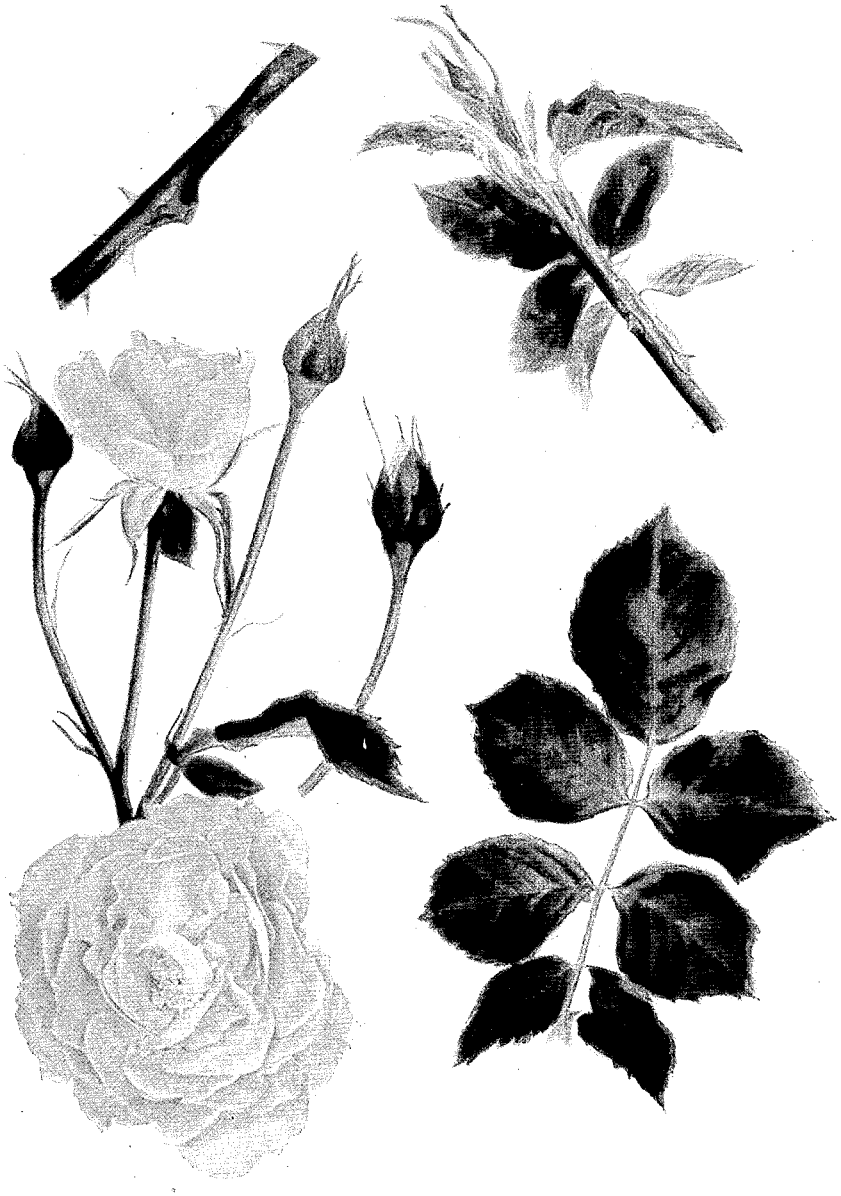
Inventor.
D. H. Morey, Jr.
By: Robb & Robb
Attorneys.

United States Patent Office

Plant Pat. 1,709
Patented May 20, 1958

1,709

ROSE PLANT

Dennison H. Morey, Jr., Pleasanton, Calif., assignor to Jackson & Perkins Company, Newark, N. Y., a corporation of New York Application September 19, 1957, Serial No. 685,055

1 Claim. (Cl. 47—61)

The present invention relates to a new and distinct variety of rose plant of the large-flowered polyantha class, which was originated by me by crossing the variety "Red Pinocchio" (Plant Patent No. 812) with the variety "Floradora" (unpatented).

The primary objective of this cross was to produce a new floribunda rose variety in which scarlet flowers having orange tones are borne on plants of dense and bushy habit having dark, shiny foliage.

This objective was fully achieved, as evidenced by the following characteristics which are outstanding in the new variety, and which distinguish it from its parents, as well as from all other varieties of which I am aware:

(1) A dense and bushy habit of plant growth;

(2) Dark, shiny foliage;

(3) A very large flower head, which is unusual in a rose of this type; and (4) The distinctive sharp Scarlet Red general color tonality of the flowers, said color being emphasized by the large flower heads.

Asexual reproduction of the new variety by budding, as performed at Newark, New York and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
*Seed parent.*—"Red Pinocchio."
*Pollen parent.*—"Floradora."

Classification:
*Botanic.*—Large-flowered polyantha.
*Commercial.*—Floribunda.

*Flower*

(Observations made from specimens grown outdoors at Newark, New York, near mid-afternoon near the middle of September.)

Blooming habit. Very large flower heads. Recurrent—continuous.

Bud:
*Size.*—Medium.
*Form.*—Globular; is not affected by wet or hot weather.
*Color.*—When sepals first divide—Scarlet Red, Plate 1. When petals begin to unfurl—Scarlet Red, Plate 1, lightly overcast with Spectrum Red, Plate 1. When half-blown; inside of petals—Spectrum Red, Plate 1, lightly overcast with Scarlet Red, Plate 1; reverse of petals—Spectrum Red, Plate 1.

*Sepals.*—Branched; curl back when petals begin to unfurl. Color: inside—Light Fluorite Green, Plate 32, with center lightly overcast with Vandyke Red, Plate 13; outside—Deep Dull Yellow-Green (1), Plate 32, lightly overcast with Acajou Red, Plate 13.
*Calyx.*—Color—Chromium Green, Plate 32. Shape—funnel. Size—small. Aspect—smooth. Odor when rubbed—none.
*Peduncle.*—Length—medium. Aspect—rough. Strength—erect; slender. Color—Light Bice Green, Plate 17.
*Opening.*—Opens up well; is not affected by adverse weather conditions.

Bloom:
*Size.*—Medium. Average size when fully expanded—3¼ inches.
*Borne.*—Several together and in flat clusters.
*Stems.*—Medium length; strong.
*Form (when first open).*—Cupped. Permanence—flattens.
*Petalage.*—Double (full but open-center). Number of petals under normal conditions—from 35 to 40.
*Color.*—Center of flower—Scarlet Red, Plate 1, lightly overcast with Spectrum Red, Plate 1. Outer petals—Scarlet Red, Plate 1. Base of petals (aiglet)—Primrose Yellow, Plate 30. Inside of petals—Spectrum Red, Plate 1, with center lightly overcast with Scarlet, Plate 1. Reverse of petals—Rose Red, Plate 12, lightly overcast with Begonia Rose, Plate 1 in center. General tonality from a distance—Spectrum Red, Plate 1.
*Discoloration.*—General tonality at end of first day—Scarlet Red, Plate 1, lightly overcast with Spectrum Red, Plate 1. Second day—Spectrum Red, Plate 1, lightly overcast with Scarlet Red, Plate 1. Third day—Spectrum Red, Plate 1.

Petals:
*Texture.*—Leathery; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few; large.
*Persistence.*—Drop off cleanly, but some hang on and dry.
*Fragrance.*—Slight. Nature—"Old Rose perfume" (centifolia).
*Lasting quality.*—On the plant—long. As cut flower—long.

*Genital organs*

Stamens, anthers: Medium size; many; regularly arranged around styles. Color—Capucine Yellow, Plate 3.
Stamens, Filaments (threads): Medium length. Color—Old Rose, Plate 13.
Pollen: Color—Pale Yellow-Orange, Plate 4.
Styles: Columnar: uneven length; medium length; thin.
Stigmas: Color—Primrose Yellow, Plate 30.
Ovaries: All enclosed in calyx.
Hips: None.
Seeds: None.

*Plant*

Form: Bush.
Growth: Vigorous; upright; compact.
Foliage: Compound of 5 to 7 leaflets.
*Size.*—Medium.
*Quantity.*—Abundant.
*Color.*—New foliage: upper side—Yellowish Oil Green, Plate 5, lightly overcast with Pomegranate Purple, Plate 12; under side—Pomegranate Purple, Plate 12. Old foliage: upper side—Varley's Green, Plate 18; under side—Light Hellebore Green, Plate 17.

*Shape.*—Oval pointed.

*Texture.*—Upper side—leathery; glossy. Under side—smooth.

*Ribs and veins.*—Ordinary.

*Edge.*—Serrated (saw-toothed).

*Serration.*—Both double and single; small.

*Leaf stem.*—Color—Yellowish Critine, Plate 16. Under side—smooth.

*Stipules.*—Medium length; smooth.

Wood:

*New wood.*—Color—Parrot Green, Plate 6. Bark—smooth.

*Old wood.*—Color—Varley's Green, Plate 18. Bark—smooth.

Thorns:

*Thorns.*—Quantity: on main stalks from base—ordinary; on laterals from stalk—ordinary. Form—flat base; medium length; hooked downward. Color (when young)—Hellebore Red, Plate 38. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by its dense and bushy habit of plant growth, its dark and shiny foliage, its very large flower heads, and the sharp Scarlet Red general color tonality of its flowers.

No references cited.